(12) United States Patent
Cornell et al.

(10) Patent No.: US 8,492,366 B2
(45) Date of Patent: Jul. 23, 2013

(54) ENHANCEDLY-SOLUBILIZED BETA-HYDROXY ACIDS AND HIGHER POTENCY SKIN PEELS FORMULATED THEREFROM

(75) Inventors: Marc Cornell, Jackson, NJ (US); Hani Fares, Somerset, NJ (US); Sidney Peter Foltis, Nutley, NJ (US); Isabelle Hansenne, Westfield, NJ (US)

(73) Assignee: Societe L'Oreal S.A., Paris (FR)

( * ) Notice: Subject to any disclaimer, the term of this patent is extended or adjusted under 35 U.S.C. 154(b) by 8 days.

(21) Appl. No.: 10/373,102

(22) Filed: Feb. 26, 2003

(65) Prior Publication Data
US 2004/0067243 A1 Apr. 8, 2004

Related U.S. Application Data

(60) Provisional application No. 60/416,259, filed on Oct. 7, 2002.

(51) Int. Cl.
| | | |
|---|---|---|
| *A01N 37/36* | (2006.01) | |
| *A01N 37/00* | (2006.01) | |
| *A61K 31/60* | (2006.01) | |
| *A61K 38/00* | (2006.01) | |
| *A61K 31/19* | (2006.01) | |
| *A61K 31/185* | (2006.01) | |
| *A61P 17/00* | (2006.01) | |

(52) U.S. Cl.
USPC ......... 514/159; 514/163; 514/18.6; 514/18.8; 514/557; 514/576; 514/844; 514/859; 514/944

(58) Field of Classification Search
USPC ............... 424/401, 78.03; 514/159, 844, 163, 514/18.6, 18.8, 557, 576, 859, 944
See application file for complete search history.

(56) References Cited

U.S. PATENT DOCUMENTS

| | | | | |
|---|---|---|---|---|
| 4,608,370 A | * | 8/1986 | Aronsohn | 514/159 |
| 4,767,750 A | * | 8/1988 | Jacquet et al. | 514/159 |
| 4,954,487 A | | 9/1990 | Cooper et al. | |
| 5,091,171 A | * | 2/1992 | Yu et al. | 424/642 |
| 5,296,476 A | | 3/1994 | Henderson | |
| 5,449,519 A | | 9/1995 | Wolf et al. | |
| 5,520,918 A | * | 5/1996 | Smith | 424/401 |
| 5,547,988 A | * | 8/1996 | Yu et al. | 514/557 |
| 5,569,651 A | | 10/1996 | Garrison et al. | |
| 5,652,266 A | | 7/1997 | Bobier-Rival et al. | |
| 5,874,463 A | * | 2/1999 | Ancira | 514/460 |
| 6,300,369 B1 | * | 10/2001 | Ancira | 514/460 |
| 6,410,036 B1 | | 6/2002 | De Rosa et al. | |

FOREIGN PATENT DOCUMENTS

| | | | |
|---|---|---|---|
| WO | 92/13529 A1 | | 8/1992 |
| WO | 97/28786 A1 | | 8/1997 |
| WO | WO 97/28786 | * | 8/1997 |
| WO | 00/02593 A2 | | 1/2000 |

OTHER PUBLICATIONS www.cop.ufl.edu/safezone/prokai/pha5100/solubility.htm (Persky et al. University of Florida, 2001).*
The Merck Index (supplied by Applicants, Edition: 1989, p. 1324, compound No. 8301: Salicylic Acid).*
Solubility supersaturated solution (retrieved online via www.dynamicscience.com.au on Jun. 10, 2011).*
Solubility as a function of temperature (power point slides date on on Jan. 25, 2009, retrieved online via Google search).*
The Merck Index, thirteenth edition, eds. M. J. O'Neil et al., pp. 1495-1496, Item No. 8411 (2001).

* cited by examiner

*Primary Examiner* — Mina Haghighatian
*Assistant Examiner* — Helen Chui
(74) *Attorney, Agent, or Firm* — Buchanan Ingersoll & Rooney, PC

(57) ABSTRACT

The solubility in solvent media, notably alcoholic media, of the beta-hydroxy acids ("BHAs"), notably the chemical skin peeling agent salicylic acid, is markedly enhanced by solubilizing same in the presence of at least one alpha-hydroxy acid ("AHA"); higher potency, more concentrated BHA skin peel products are thus formulated.

8 Claims, No Drawings

ENHANCEDLY-SOLUBILIZED BETA-HYDROXY ACIDS AND HIGHER POTENCY SKIN PEELS FORMULATED THEREFROM

CROSS-REFERENCE TO PROVISIONAL APPLICATION

This application claims benefit of U.S. Provisional Application No. 60/416,259, filed Oct. 7, 2002, hereby expressly incorporated by reference.

BACKGROUND OF THE INVENTION

1. Technical Field of the Invention

The present invention relates to enhancing the solubility in solvent media, notably alcoholic media, of the beta-hydroxy acids ("BHAs"), notably the chemical skin peel salicylic acid, by intimately admixing same with at least one alpha-hydroxy acid ("AHA"), for example lactic acid, glycolic acid, citric acid, and the like.

This invention also relates to the formulation of higher potency BHA skin peel products, advantageously formulated as gels.

2. Description of the Prior Art

It is known to this art that the beta-hydroxy acids such as salicylic acid exhibit keratolytic activity in the skin and are useful superficial chemical skin peels. Compare WO 97/28786 and references cited therein, each of which hereby being expressly incorporated by reference. Cf. U.S. Pat. Nos. 4,954,487, 5,296,476, 5,449,519 and 6,410,036.

Salicylic acid, or 2-hydroxybenzoic acid, has the structural formula:

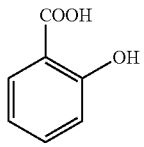

and its maximum solubility in alcohol is roughly on the order of 29%. It is described in the 13$^{th}$ Edition of the Merck Index (2001) at pages 1495-1496, Item No. 8411 (also expressly incorporated by reference), as are various of the clinical indications thereof, e.g., treatment of warts and corns, acne, as an anti-inflammatory, analgesic, antipyretic.

WO 97/28786 describes a method for effecting a superficial chemical skin peel by topically applying to skin to be treated, usually facial skin, a composition containing at least 15% by weight of salicylic acid, in a dermatologically acceptable liquid solvent.

Such superficial chemical skin peels are useful for the treatment of a variety of skin disorders, for example photodamaged skin, hyperpigmentation, acne vulgaris, rosacea, premalignant skin cancer, wrinkles and fine lines, superficial scars and the like.

While WO 97/28786 mandates salicylic acid concentrations of at least 15% by weight, even suggesting "most preferably . . . at least 30 wt. %," to provide the desired efficacy, such concentrations are nonetheless limited to the saturation concentration of the salicylic acid in the particular solvent.

Need, therefore, continues to exist for even more concentrated BHA chemical skin peels.

SUMMARY OF THE INVENTION

It has now unexpectedly and surprisingly been determined that one family of acids, the alpha-hydroxy acids (AHAs), enhances/increases the solubility of another family of acids, the beta-hydroxy acids (BHAs), in solvent media therefor, particularly in alcoholic solvent media.

The present invention thus features higher potency, more concentrated BHA skin peel cosmetic/dermatological compositions, as well as a chemical skin peel regime or regimen including topical application onto the skin of a thus effective amount of the subject cosmetic/dermatological compositions.

DETAILED DESCRIPTION OF BEST MODE AND SPECIFIC/PREFERRED EMBODIMENTS OF THE INVENTION

More particularly according to the present invention, unique methodology/technique is provided for increasing/enhancing the solubility of the BHAs in solution, particularly in alcoholic solution.

Specifically, it has now been determined that intimately admixing and dissolving one family of hydroxy acids, the AHAs, with another family of hydroxy acids, the BHAs, will increase/enhance the solubility of the latter in a solvent medium, particularly an alcoholic solvent medium.

As regards the keratolytic activity of the beta-hydroxy acids such as salicylic acid in the skin, the activity of such molecules is limited by their solubilities in the delivery vehicle. Enhancing or increasing the solubility limits of the BHAs is therefore a desideratum for the drug delivery chemist and formulator.

To date, however, upon review of the scientific and patent literature, it will be seen that those skilled in this art approached this solubility problem via traditional scientific methodology such as including co-solvents, surfactants, formulating eutectic mixtures, etc.

As aforesaid, need continues to exist for yet improved regime for increasing/enhancing the solubility of the BHAs in solvent/alcoholic solution.

The subject AHA/BHA approach has unexpectedly enhanced/increased the levels of the BHA that can be attained in a variety of cosmetic and dermatological preparations, notably higher potency BHA skin peel products, and also provides for the enhanced drug delivery of the BHAs.

While not wishing to be bound to or by any particular theory or explanation, consider salicylic acid and lactic acid as representative BHA and AHA molecular species. When relatively polar BHA molecules such as salicylic acid (ortho-substituted benzoic acid) are dissolved in polar solvents such as water or alcohols, their solvation with such solvents is quite high due to the formation of multiple hydrogen bonds. The addition of a smaller polar AHA molecule, e.g., lactic acid, is believed to disrupt the hydrogen bonding network formed between the solvent and solute and promote a change in solubility. Too, the lactic acid might even complex with salicylic acid through hydrogen bond formation, thus forming complexes that have a higher solubility than that of salicylic acid. Hence, the overall solubility of salicylic acid is enhanced/increased.

The AHAs and BHAs well suited for formulating the cosmetic/dermatological compositions of the present invention, in particular for formulating higher potency BHA skin peel gels, are those described in the several patents issued to Van Scott and Yu, for example their U.S. Pat. No. 5,091,171 (also expressly incorporated by reference), including, inter alia, lactic acid, glycolic acid, citric acid, salicylic acid, etc. Per Van Scott/Yu, the generic structure of the alpha-hydroxy acids, themselves useful chemical skin peel agents, is as follows:

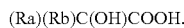

The corresponding structure of the beta-hydroxy acids, thus, would be:

(Ra)(Rb)C(OH)CCOOH.

Representative alcoholic solvent media for the AHAs and BHAs include the polyethylene glycols, a propylene glycol (e.g., glycerol), ethanol, a butylene glycol, and the like. These are all topically applicable and cosmetically/dermatologically acceptable.

The subject higher potency BHA skin peels are topically applied onto that area of the skin requiring such treatment (regime or regimen) for such period of time as required to elicit the desired cosmetic/dermatological effect, namely, for treating those skin disorders described in WO 97/28786.

Advantageously, the cosmetic/dermatological compositions or solutions according to the invention contain from 1% to 50% of BHA, preferably from 10% to 40% and more preferably from 30% to 35%. The corresponding amounts of AHA advantageously range from 1% to 20%, preferably from 2% to 15% and more preferably from 3% to 8%. The subject cosmetic/dermatological compositions may be liquid, e.g., lotions, semisolid, or solids. Most advantageously they include a gelling agent and are formulated as gels.

The subject compositions may also contain minor amounts of the usual cosmetic/dermatological additives and adjuvants, so long as they do not adversely affect the desired property of the AHA/BHA combination. Exemplary such additives and adjuvants include preservatives, stabilizers, antioxidants, surfactants, fragrances, colorants, etc.

In order to further illustrate the present invention and the advantages thereof, the following specific examples are given, it being understood that same are intended only as illustrative and in nowise limitative.

In said examples to follow, all parts and percentages are given by weight unless otherwise indicated.

EXAMPLE 1

Formulation of Solutions of Salicylic Acid in Glycerol to Compare Solubility Determinations Procedure: the Following Solutions were Prepared:
Preparation A:
Two (2) grams of salicylic acid were dissolved in 120 ml of glycerol.
Preparation B:
2.2 grams of salicylic acid plus 3 grams of glycolic acid (crystals) were dissolved in 120 ml of glycerol.

For each preparation, the respective constituents were mixed at room temperature until dissolved. Both solutions were hazy after three (3) hours of mixing. Each solution was then warmed to 40° C. and, after two (2) hours of further mixing, each solution was clear and remained so after an additional twenty-four (24) hours has elapsed.

This example confirms the solubility values for salicylic acid reported in the literature (for example, in the Merck Index), and also evidences that Preparation B exceeds these values of maximum salicylic acid solubility by at least 10%.

EXAMPLE 2

Formulation of a Higher Potency Chemical Skin Peel Gel

Procedure
In a Caframo mixer fitted with a propeller blade, glycolic acid and salicylic acid were dissolved in 200 proof denatured ethanol under mixing at a temperature maintained from 25° to 35° C.

When a clear solution was obtained, the gelling agent (hydroxypropyl cellulose-"KLUCEL" marketed by Hercules) was dispersed therein and mixing was continued until a uniform gel was produced.

The composition of the gel, which is well suited as a superficial chemical skin peel, was as follows:

| | % |
|---|---|
| Ethanol | 63.000 |
| Salicylic Acid | 32.000 |
| KLUCEL HF | 2.000 |
| Glycolic Acid (crystals) | 3.000 |
| | 100.00 |

| | 200 G |
|---|---|
| Ethanol | 126.000 |
| Salicylic Acid | 64.000 |
| Klucel HF | 4.000 |
| Glycolic Acid (crystals) | 6.000 |
| | 200.00 |

EXAMPLE 3

Formulation of High Potency Skin Peel Gels with Various Polymers and Viscosity Evaluations thereof Skin peel gels having the following compositions were formulated:

| Ingredients | A % | B % | C % |
|---|---|---|---|
| Polyethylene Glycol 300 | 67.000 | 67.000 | 67.000 |
| Salicylic Acid | 30.000 | 30.000 | 30.000 |
| ULTREZ 980 (Noveon) | 3.000 | 0.000 | 0.000 |
| PERFORMAX 10 (Noveon) | 0.000 | 3.000 | 0.000 |
| CARBOPOL 450 (New Phase) | 0.000 | 0.000 | 3.000 |
| | 100.000 | 100.000 | 100.000 |

Hazy to transparent viscous pourable gels were thus produced.

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:
1. A topically applicable cosmetic/dermatological skin peel composition consisting essentially of 30 to 35% by weight of a beta-hydroxy acid (BHA) dissolved in a cosmetically/dermatologically acceptable solvent medium therefor, said BHA being present in said solvent medium in a supersaturated amount in excess of the otherwise saturation con- centration therein, said solvent medium also containing 3 to 8% by weight of at least one alpha-hydroxy acid (AHA) effective to attain supersaturation solubilization of such amount of BHA above the saturation concentration thereof in said solvent medium therefor.

2. The cosmetic/dermatological composition as defined by claim 1, said solvent medium comprising an alcoholic solvent medium.

3. The cosmetic/dermatological composition as defined by claim 2, said BHA comprising salicylic acid and said at least one AHA comprising lactic acid, glycolic acid and/or citric acid.

4. The cosmetic/dermatological composition as defined in claim 2, said alcoholic solvent medium comprising a polyethylene glycol, a propylene glycol, ethanol or a butylene glycol.

5. The cosmetic/dermatological composition as defined by claim 1 further containing a cellulosic gelling agent.

6. The cosmetic/dermatological composition as defined by claim 1, in the form of a gel.

7. A chemical skin peel regime or regimen including topical application onto the skin the cosmetic/dermatological composition of claim 1.

8. The chemical skin peel regime or regimen as defined by claim 7 comprising treating photodamaged skin, hyperpigmentation, acne vulgaris, rosacea, wrinkles, fine lines or superficial scars.

* * * * *